United States Patent [19]

Pachence et al.

[11] Patent Number: 5,713,374

[45] Date of Patent: Feb. 3, 1998

[54] FIXATION METHOD FOR THE ATTACHMENT OF WOUND REPAIR MATERIALS TO CARTILAGE DEFECTS

[75] Inventors: James M. Pachence, Hopewell, N.J.; Sally Frenkel, Flushing; David Menche, New York, both of N.Y.

[73] Assignee: The Hospital for Joint Diseases Orthopaedic Institute, New York, N.J.

[21] Appl. No.: 386,799

[22] Filed: Feb. 10, 1995

[51] Int. Cl.$^6$ ................................................. A61B 19/00
[52] U.S. Cl. ................................................. 128/898; 623/11
[58] Field of Search ..................... 128/897–98; 623/11, 623/13, 16; 602/42, 43, 53, 79; 606/151, 213, 215, 233

[56] References Cited

U.S. PATENT DOCUMENTS

| | | |
|---|---|---|
| 4,458,678 | 7/1984 | Yannas et al. |
| 4,505,266 | 3/1985 | Yannas et al. |
| 4,846,835 | 7/1989 | Grande . |
| 5,133,755 | 7/1992 | Brekke ................................. 623/16 |
| 5,206,028 | 4/1993 | Li ........................................ 424/484 |
| 5,312,435 | 5/1994 | Nash et al. ......................... 606/215 |
| 5,531,759 | 7/1996 | Kensey et al. ..................... 606/215 |

OTHER PUBLICATIONS

Ahmad, Frenkel, Casar, and Alexander; A mechanical testing technique for articular cartilage; a study of intrinsic repair, In: Advances in Bioengineering (Bidez, ed.) ASME, New York, pp. 245–251, 1991.

Amiel, Coutts, Harwood, Ishiuze, and Kleiner; The Chondrogenesis of Rib Periochondrial Grafts for Repair of Full Thickenss Articular Cartilage Defects in a Rabbit Model, Connective Tissue Research 18:27–39 (1988).

Athanasiou, Schmitz, Schenck, Clem, Aufdermorte, Boyan; The Use of Biodegradable Implants for Repairing Large Articular Cartilage Defects in the Rabbit. Transactions of the 38th Annual Meeting of the ORS, p. 172, (1992).

Billings, von Schroeder, Mai, Aratow, Amiel, Woo, and Coutts; Cartilage resurfacing of the rabbit knee. Acta Orthop. Scand. 61(3); 201–206 (1990).

Convery, Akeson, Keown; The Repair of Large Osteochondral Defects, Clinical Orthopedics and Related Research 82:253–262 (1972).

Dahlberg and Kreicbergs; Demineralized Allogeneic Bone Matrix for Cartilage Repair, J. Orthop. Research 9:11–19 (1991).

Grande, Pitman, Peterson, Menche and Klein: The repair of experimentally produced defects in rabbit articular by autologous chondrocyte transplantation. Journal of Orthopedic Research 7:208–218 (1989).

Homminga, Bulstra, Bouwmeester and Van Der Linden; Perichondral Grafting for Cartilage Lesions of the Knee. The Journal of Bone and Joint Surgery 72:1003–1007 (1990).

Kimura, Yasui, Ohsawa and Ono; Chondrocytes Embedded in Collagen Gels Maintain Cartilage Phenotype During Long–Term Cultures. Clinical Orthopaedics 186:231–239 (1984).

Moran, Kim, Slater; Biological Resurfacing of Full–Thickenss Defects in Patellar Articular Cartilage of the Rabbit. Journal of Bone and Joint Surgery 74:659–667 (1992).

Nixon, Sams, Minor; Long–term Survival and Neocartilage Maturation Following Extensive Articular Resurfacing With Chondrocyte Laden Collagen Scaffolds, Transactions of the 40th Annual Meeting of the ORS, 1994.

(List continued on next page.)

*Primary Examiner*—John P. Lacyk
*Attorney, Agent, or Firm*—Caesar, Rivise, Bernstein, Cohen & Pokotilow, Ltd.

[57] ABSTRACT

An attachment method to hold a biomaterial in place until healing occurs. The method consists of anchoring sutures through the subchondral plate into bony tissue with at least two lines emerging from the surface. The anchored suture lines are then pulled through the implant at its four quadrants, and is thus used to secure the cartilage repair material into the wound site.

11 Claims, 2 Drawing Sheets

OTHER PUBLICATIONS

Nixon, Sams, Lust, Grande and Mohammed; Temporal Matrix Synthesis and Histological Features of a Chondrocyte-Laden Porous Collagen Cartilage Analogue, American Journal of Veterinary Research 54:349-356 (1993).

Nixon, Lust and Vernier-Singer; Isolation, Propagation, and Cryopreservation of Equine Articular Chondrocytes. American Journal of Veterinary Research 53:2364-2370 (1992).

von Schroder, Kwan, Amiel and Coutts: The Use of Polylactic Acid Matrix and Periosteal Grafts for the Reconstruction of Rabbit Knee Articular Defects. Journal of Biomedical Materials Research 25:329-339 (1991).

Vachon, McIlwraith, Powers, McFadden and D.Amiel: Morphologic and Biochemical Study of Sternal Cartilage Autographs for Resurfacing Induced Osteochondral Defects in Horses. American Journal of Veterinary Research 53:1039-1047 (1992).

Weadock, Olson, and Silver: Evaluation of Collagen Crosslinking Techniques. Biomat, Med. Dev., Art, Org., 11(4), 293-318 (1983-84).

Homminga, Bulstra, Kuijer and Anton J. van der Linden: Repair of sheep articular cartilage defects with a rabbit costal perichondrial graft. Department of Orthopedics, University Hospital Masstricht, The Netherlands.

Robinson: Histologic Study of Articular Cartilage Repair in the Marmoset Condyle. J. Oral Maxillofac Surg. 51:1088-1094, 1993.

Grande, Singh and Pugh. Healing of Experimentally Produced Lesions in Articular Cartilage Following Chondrocyte Transplantation. The Anatomical Record 218:142-148 (1987).

FIXATION METHOD FOR THE ATTACHMENT OF WOUND REPAIR MATERIALS TO CARTILAGE DEFECTS

FIELD OF THE INVENTION

This invention is within the technical fields of surgery, medicine, tissue engineering, biology, biomaterials, polymers, and biochemistry. It is both a product and a method of use for the repair of cartilage lesions, with and without the use of chondrocytes cultured in vitro.

BACKGROUND

It has been well documented that injured articular cartilage has only a limited ability for self-repair. As articular cartilage is relatively avascular and aneural, loss of the surface tissue will result in a permanently scarred site; lesions which fracture the subchondral bone which has a greater vascular supply will undergo an inflammation/repair response, with the damaged site filing with fibrocartilage tissue (Convery, et al. 1972). In either case, function is impaired and chronic pain is the usual prognosis as the biochemical and biomechanical characteristics of the cartilage have been altered. Current treatment protocols call for surgical intervention (such as abrasion arthroplasty, excision and drilling, articular cartilage debridement, and arthroscopic shaving) and will most often lead again to inadequate repair. Long-term morbidity such as degeneration to arthritic conditions will often result in patients with chronic cartilage problems.

Nevertheless, articular cartilage theoretically does have some intrinsic ability to heal after injury. For example, chondrocytes are capable of replication when isolated enzymatically from the cartilage matrix (Grande, et al. 1989). It has been suggested that cartilage repair can be initiated by either replication of chondrocytes in the regions adjacent to the defect, or by metaplasia of chondrocytes from other connective tissue stem cells within the joint capsule, such as from the synovium and subchondral bone (Sokoloff, 1978). Given this possibility, investigations of autograft or allograft tissue and tissue analogues to heal cartilage lesions has progressed.

Techniques were developed to utilize autologous tissue, such as transplantation of: 1) osteochondral grafts (DePalma, et al. 1963); 2) chondrocytes (Grande, et al. 1989); 3) periosteum (Homminga, et al., 1990); and 4) demineralized bone (Dahlberg and Kreicbers, 1991). These techniques have been used to transplant whole or partial joints, with mixed results. For example, a number of investigators attempted to heal cartilage defects using chondrocytes isolated from epiphysial plates, as well as articular cells, with the hypothesis that these cells would have a greater chance of success due to their heightened metabolism (Itay, et al. 1987). Clinical studies using cultured cells reported excellent results, showing a significant decrease in pain and restoration of normal function after two to four years post-op (Iloika, et al. 1990; Ilomminga, et al. 1990).

Other investigators have used a combination of materials and autologous tissue to effectively repair cartilage defects, such as: 1) demineralized bone with perichondrium (Billing, et al., 1990) 2) polylactic acid matrices and periosteal graft (von Schroeder, et al. 1991); and 3) bioresorbable meshes and chondrocytes (Freed, et al. 1993). Although these approaches gave repair tissue that more closely resembled normal cartilage than either the unfilled sites, or the sites filled with materials alone, it was evident that there was again a substantial amount of fibrocartilage formation.

To date, the limited success of articular cartilage repair is in part due to the lack of suitable methods for internal surgical fixation. The initial technique used by Grande, et al. 1989, calls for suturing a periosteal flap into place. A piece of periosteum was freshly isolated from the proximal tibia, and sutured to the periphery of the patella defect with 9-0 Vicryl sutures. This technique has been found to be surgically cumbersome, and limiting with respect to the size and placement of the defect. A number of authors have used a press fit technique to secure an implant into a cartilage defect site (e.g., Coutts, et al. 1994; Freed, et al. 1993; Nixon, et al. 1994). While this technique may work in non-weight bearing conditions, it is possible that the implant can dislodge during motion, especially during the first two weeks after implantation. In addition, there is limited flexibility to adjust the height of the implant with respect to the articular cartilage surface using a press fit technique.

OBJECTS OF THE INVENTION

Accordingly, it is a general object of this invention to provide a method of securing a multi-staged collagen implant to repair cartilage lesions which overcomes the disadvantages of the prior art.

It is a further object of this invention to provide a method of securing a multi-staged collagen implant to repair cartilage lesions which is effective and safe.

It is another object of this invention to provide method of securing a multi-staged collagen implant to repair cartilage lesions which have resorbable components.

SUMMARY OF THE INVENTION

An attachment method is used to hold a cartilage repair template into a cartilage defect site. The method consists of the steps of anchoring sutures through the subchondral plate into bony tissue, with two or more lines emerging from a surface thereof. The anchored suture lines are used to secure the cartilage repair template to the site.

DESCRIPTION OF THE DRAWINGS

Other objects and many attendant features of this invention will become readily appreciated as the same becomes better understood by reference to the following detailed description when considered in connection with the accompanying drawings wherein.

1 representing the articular surface, 2 hyaline cartilage 3 cancellous bone and marrow, 4 defect, 5 extracellular matrix, 6 chondrocytes, 7 tidemark, 8 calcified cartilage and 9 the subchondral plate.

Figure 1:
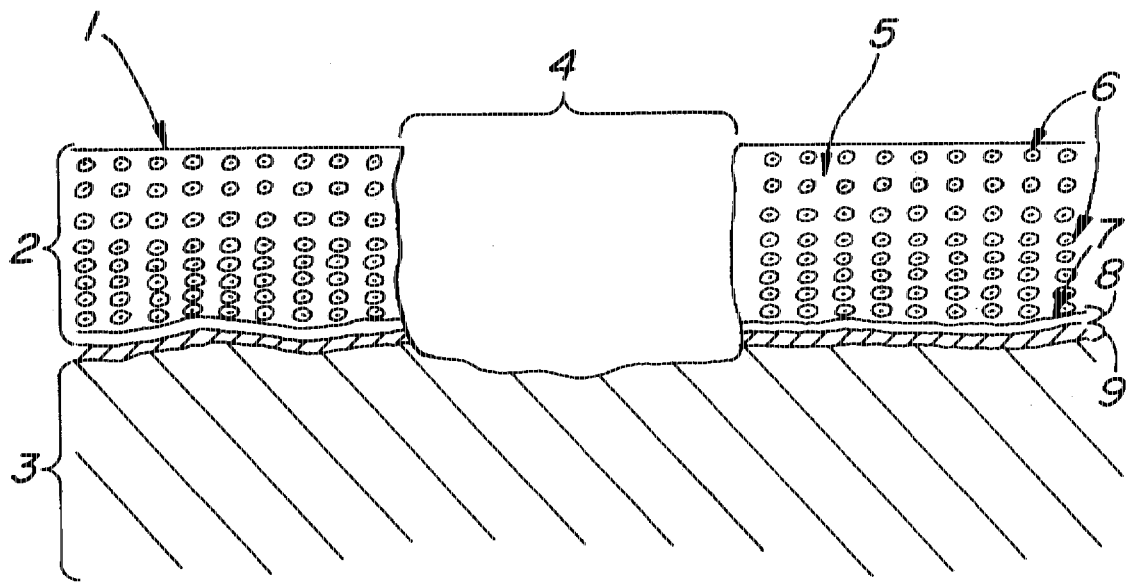
FIG. 1 shows the anatomy of normal cartilage and a defect or wound site 4 in which the following reference characters appear.
Figure 2:
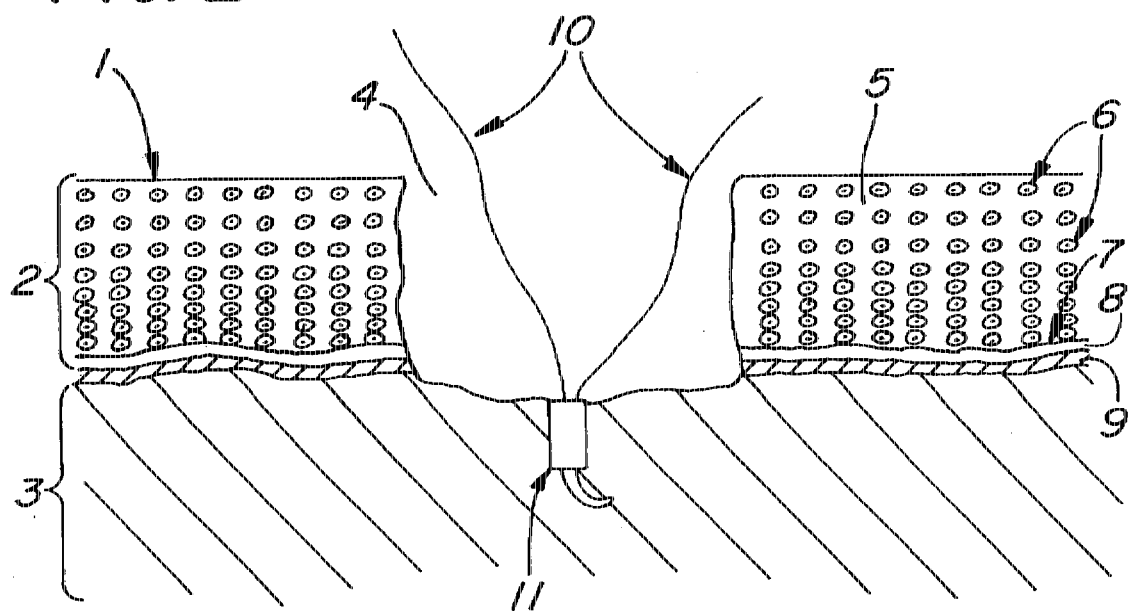

FIG. 2 shows an anchor 11 with attached suture lines 10 embedded into the bone 3 at the defect site 4.

Figure 3:
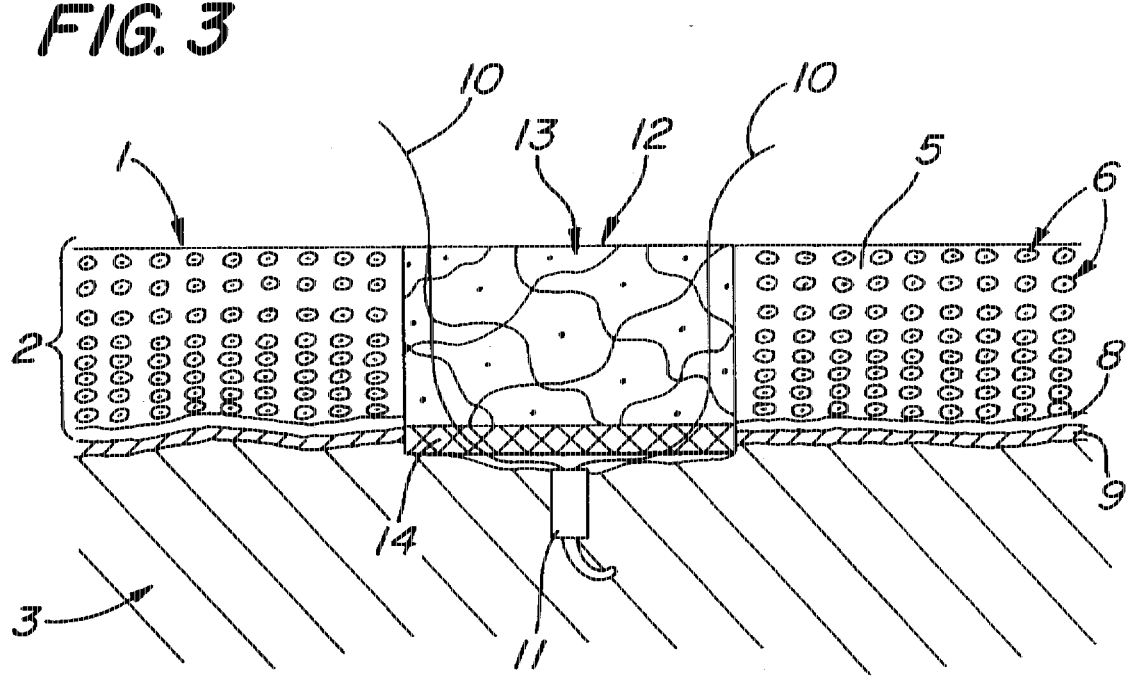

FIG. 3 shows the positioning of the collagen template 12 with the porous collagen matrix 13 and the dense collagen membrane 14 in threading the anchored sutures 10 through the template 12.

Figure 4:
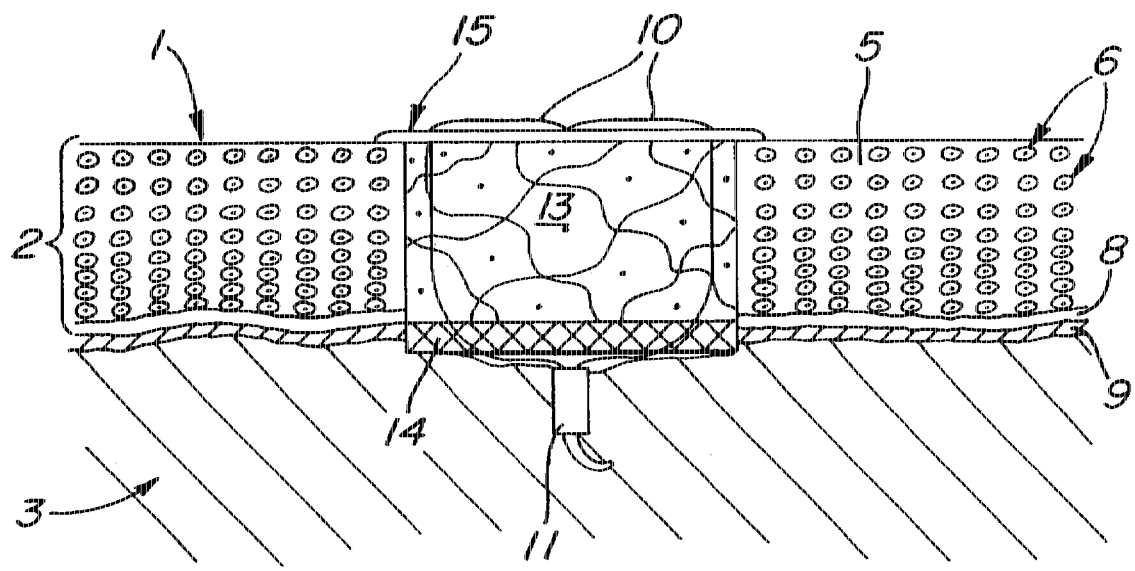

FIG. 4 shows the positioning of a top protective layer 15 in securing this layer 15 and template 12 with anchoring sutures 10.

DESCRIPTION OF THE PREFERRED EMBODIMENTS

The advantage of the anchoring invention is that it secures an implant 12 to the site 4 of cartilage regeneration and prevents migration, as demonstrated in a canine model of cartilage repair under load-bearing conditions. Preventing migration is important because not only is the tissue regeneration aspect of the implant required at the site, but also because the biomechanics of the joint would not be disrupted by an object that partly or totally obstructs smooth motion of the joint. Another advantage of the invention is that it overcomes the press-fit size limitation of the defect to be treated.

Anchors have been used in the past to secure soft tissue to bone, particularly muscle, ligaments, and tendon in and around joints. The anchors are made from biocompatible metals and plastics and are available in a variety of sizes. It was found that suture materials can be secured to the distal aspect of the anchor, prior to placing the anchor into the defect site. A drill hole, is made at the approximate center of the defect. The anchor is then set into the prepared site, allowing the suture lines to freely extend away from the articular surface of the joint.

EXAMPLES OF INVENTION USE

1. Prepare a surgically defined site 4, slightly smaller than the size of the cartilage repair implant or template 12.

2. Drill an appropriately sized hole, (e.g., 1 mm in diameter) approximately in the center of the defect site 4. The hole should be of a sufficient diameter to allow the anchor 11 to be set into place and to permit the passage of a suture 10 therethrough.

3. Attach the appropriate number of sutures 10, e.g., two sutures to an anchor 11 (e.g., product sold as product number Mitek No. 210193 G-II MINI ANCHOR, sold by Mitek Surgical Products, Inc., Norwood, Mass., as also disclosed in U.S. Pat. Nos. 4,898,156 and 4,946,468, the entire disclosures of which are incorporated by reference herein), so that equal sized strands emanate from the distal aspect of the anchor 11, e.g., four. The sutures 10 should be bioresorbable, and should be sized 5-0 or less.

4. Set the anchor 11 into the drill hole, so that the resorbable suture strands 10 protrude from the center of the surgically prepared site, e.g., four (FIG. 2).

5. Pull the suture lines through the cartilage repair implant 12 (FIG. 3).

6. Tie the sutures so that the knot is buried beneath the implant surface or beneath the protective cover, if utilized), and not exposed to the articular surface 1 (FIG. 4).

Defects in articular cartilage can be healed by utilizing a regeneration template formed by combining a porous collagen sponge ("collagen matrix") with a dense collagen membrane as described in our copending application entitled A Multi-staged Collagen-Based Template Or Implant For Use In The Repair of Cartilage Lesions, the entire disclosure of which is incorporated by reference herein. The dense collagen matrix is made with a pore size of less than 1 micrometer, and is cross-linked with a non-cytotoxic agent to increase strength and lengthen resorption time. Because of this dense collagen membrane, the invention can be used in full-thickness defects, including those which traverse the subchondral plate. The dense collagen membrane is placed on the surface of the cartilage defect to prevent cell migration from the subchondral plate and vasculature. The collagen membrane will allow movement and exchange of fluids, nutrients, cytokines and other factors necessary for cartilage regeneration. The thicknesses of the components of the template 12 can vary depending upon the circumstances of use. For example, the thickness of the dense collagen membrane may be in the range of 50 to 200 micrometers or more and the thickness of the porous collagen matrix may be in the range of 0.5 to 8 millimeters or more.

The collagen matrix component of that template has been developed to allow attachment and growth of cells, particularly chondrocytes. In vitro studies have been used to determine the optimal pore size of the porous collagen matrix component of the template. The collagen matrix can be used to immobilize chondrocytes in vitro and support subsequent cell growth. The cell number can then be expanded in vitro, and the collagen matrix can be used to transport the cells to the repair site and retain the cells in position following implantation.

Previous studies have shown that the collagen matrix pore size can be controlled by varying the dispersion pH, collagen concentration and the lyophilization cycle (freezing time, temperature range, and cycle time (Dillion et al. 1986)). The collagen matrices have also been characterized according to their permeability to globular macromolecules. For example, it was found that a pore structure of approximately 15 micrometers would exclude molecules greater than $10^6$ daltons; a dense collagen membrane had a molecular weight exclusion of $7 \times 10^4$ daltons (Li, 1987). Chondrocytes were grown on type I collagen matrices of varied pore structure in order to determine the effect of the average matrix pore size on cellular growth rate. It was found that the pore structure did not affect the rate of cell growth after 12 days. However, chondrocyte infiltration was greater for average pore sizes greater than 100 micrometers. A parallel study using fibroblasts showed similar cell growth results. It is important to note that the growth rate of fibroblasts on the dense collagen membrane was approximately the same as a porous matrix, but that migration of cells through the membrane was excluded (Pachence et al., 1991).

The dense collagen membrane can be attached to the collagen matrix prior to cell culture or prior to implantation, using: 1) bioresorbable sutures; or 2) a fusing technique, requiring that the dense collagen membrane be incorporated into the collagen matrix during formation.

It has been shown through a series of in vivo studies that the template with and without the addition of chondrocytes promotes the healing of surgically induced full thickness defects in a rabbit model of cartilage damage. The chondrocyte-seeded templates have been proven, through the use of histologic, biochemical, and mechanical analyses of retrieved implant-tissue sites, to result in repair tissue which appears to be hyaline cartilage. The orientation of the template in the cartilage defect is fundamental to achieve a successful result. The dense layer is place "downward" into the defect, contacting bone, and the porous layer lies in the place of the natural cartilage. The dense layer has been shown experimentally to inhibit the formation of fibrocartilage.

Without further elaboration the foregoing will so fully illustrate our invention that others may, by applying current or future knowledge, adapt the same for use under various conditions of service.

We claim:

1. An attachment method used to hold a cartilage repair template into a cartilage defect site, the method comprising the steps of:

(a) anchoring sutures through the subchondral plate into bony tissue, in said defect site, with at least two lines emerging from a surface thereof; and (b) using the anchored suture lines to secure the cartilage repair template to the site and wherein the template includes a dense collagen membrane which is positioned closely adjacent to or against said subchondral plate.

2. The method of claim 1 additionally comprising the further step of selecting the cartilage repair template to be a bilayer material for the repair of cartilage defects leading to the regeneration of hyaline-like cartilage, comprising:

a) a first layer comprising a dense collagen membrane having a pore size of less than 1 micrometer which is cross-linked with a non-cytotoxic agent to increase strength and lengthen resorption time, to provide a barrier against movement of cells from the subchondral plate, the membrane being sufficiently permeable to allow the passage therethrough of fluids, nutrients, cytokines, and other endogenous factors necessary for healing; and b) a second layer secured to the first layer and comprising a porous collagen matrix having a pore size of 50 to 200 micrometers, which permits the ingrowth of cells; and c) positioning said cartilage repair template in said defect site, such that said dense collagen membrane is located closely adjacent to or in contact with said subchondral plate.

3. The method of claim 2 additionally comprising the step of selecting the template to comprise autologous periosteum placed on top of the collagen matrix and the matrix is initially devoid of cells.

4. The method of claim 2 additionally comprising the step of selecting the template to comprise a collagen film placed on top of the collagen matrix and the matrix is initially devoid of cells.

5. The method of claim 2 additionally comprising the step of selecting the template to comprise chondrocyte cells cultured ex vivo with the porous collagen matrix so that the chondrocytes permeate the collagen matrix.

6. The method of claim 2 additionally comprising the step of selecting the template to comprise a piece of autologous periosteum placed on top of the collagen matrix containing the chondrocyte cells.

7. The method of claim 2 additionally comprising the step of selecting the template to comprise a collagen film placed on top of the collagen matrix containing the chondrocyte cells.

8. The method of claim 2 additionally comprising the step of attaching the dense collagen membrane to the collagen matrix using a resorbable suture.

9. The method of claim 2 additionally comprising the step of applying the dense collagen membrane to the collagen matrix during formation of the bilayer material.

10. The method of claim 2 additionally comprising the step of selecting the dense collagen membrane to have a thickness in the range of 50 to 200 micrometers.

11. The method of claim 2 additionally comprising the step of selecting the porous collagen matrix to have a thickness in the range of 0.5 to 8 millimeters.

\* \* \* \* \*